(12) United States Patent
Alhuwaish et al.

(10) Patent No.: US 9,987,111 B1
(45) Date of Patent: Jun. 5, 2018

(54) OCCLUSAL CANTING IDENTIFYING TOOL

(71) Applicant: KING SAUD UNIVERSITY, Riyadh (SA)

(72) Inventors: Hessah Abdullah M. Alhuwaish, Riyadh (SA); Khalid Abdulrahman A. Almoammar, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days. days.

(21) Appl. No.: 15/587,330

(22) Filed: May 4, 2017

(51) Int. Cl.
*A61C 19/05* (2006.01)
*A61C 19/045* (2006.01)
*A61C 19/04* (2006.01)

(52) U.S. Cl.
CPC .............. *A61C 19/05* (2013.01); *A61C 19/04* (2013.01); *A61C 19/045* (2013.01)

(58) Field of Classification Search
CPC ........ A61C 19/05; A61C 19/04; A61C 19/045
See application file for complete search history.

(56) References Cited

U.S. PATENT DOCUMENTS

| 1,662,670 | A | * | 3/1928 | Harter ..................... | A61B 5/107 |
| | | | | | 33/514 |
| 2,475,706 | A | * | 7/1949 | Jamieson ............... | A61C 19/04 |
| | | | | | 33/513 |
| 2,491,136 | A | * | 12/1949 | Salzmann .............. | A61B 5/103 |
| | | | | | 33/341 |
| 3,336,670 | A | | 8/1967 | Heydenreich | |
| 3,745,665 | A | * | 7/1973 | Shilliday ................ | A61C 19/04 |
| | | | | | 33/514 |
| 3,854,208 | A | * | 12/1974 | Arant .................... | A61C 19/045 |
| | | | | | 433/73 |
| 4,034,475 | A | * | 7/1977 | Lee ....................... | A61C 11/022 |
| | | | | | 433/214 |
| 4,096,637 | A | * | 6/1978 | Stade .................... | A61C 19/045 |
| | | | | | 33/334 |
| 4,242,087 | A | * | 12/1980 | Lee ....................... | A61C 11/022 |
| | | | | | 433/54 |
| 4,261,696 | A | * | 4/1981 | Hobo .................... | A61C 19/045 |
| | | | | | 433/73 |
| RE31,716 | E | * | 10/1984 | Lee ....................... | A61C 11/022 |
| | | | | | 433/56 |

(Continued)

FOREIGN PATENT DOCUMENTS

GB            1013206       12/1965

*Primary Examiner* — Cris L Rodriguez
*Assistant Examiner* — Hao D Mai
(74) *Attorney, Agent, or Firm* — Richard C. Litman

(57) ABSTRACT

The occlusal canting identifying tool includes a frame having an elongated horizontal portion and a pair of parallel side arms movably attached to the horizontal portion at opposite ends thereof. The tool further includes a vertical arm centrally positioned on the front of the horizontal portion and a measuring assembly positioned on the rear of the horizontal portion. The measuring assembly includes a protractor rotatably attached to the rear of the horizontal portion, the protractor being configured to rotate on a horizontal axis in relation to the horizontal portion, and a bite plate connected to the protractor, the bite plate being adjustable forward and backward in relation to the protractor. The patient is instructed to bite on the bite plate, and if occlusal canting is present, the degree of canting is quantified by rotation of the protractor.

4 Claims, 4 Drawing Sheets

(56) References Cited

U.S. PATENT DOCUMENTS

| | | | | |
|---|---|---|---|---|
| 4,762,491 A | * | 8/1988 | Bolton | A61C 19/04 33/514 |
| 4,979,312 A | * | 12/1990 | Wool | A61C 7/02 33/513 |
| 5,078,600 A | * | 1/1992 | Austin | A61C 19/045 433/69 |
| 5,176,515 A | | 1/1993 | Andrews | |
| 5,738,515 A | * | 4/1998 | Leever | A61C 11/00 433/55 |
| 6,564,464 B1 | * | 5/2003 | Keating | A61B 5/1071 33/464 |
| 6,616,449 B1 | * | 9/2003 | Rocher | A61C 11/02 433/55 |
| 7,762,810 B2 | * | 7/2010 | Sildve | A61C 9/0006 433/56 |
| 8,992,217 B2 | | 3/2015 | Cho | |
| 9,072,575 B1 | * | 7/2015 | Alotaibi | A61C 19/04 |
| 2002/0032449 A1 | | 3/2002 | Rota et al. | |
| 2013/0084537 A1 | * | 4/2013 | Cho | A61C 19/045 433/29 |
| 2013/0084538 A1 | * | 4/2013 | Cho | A61C 19/045 433/29 |
| 2014/0379356 A1 | * | 12/2014 | Sachdeva | A61C 7/002 705/2 |
| 2015/0327967 A1 | | 11/2015 | Baaske et al. | |
| 2016/0250006 A1 | * | 9/2016 | Fisker | A61C 9/0046 433/213 |

\* cited by examiner

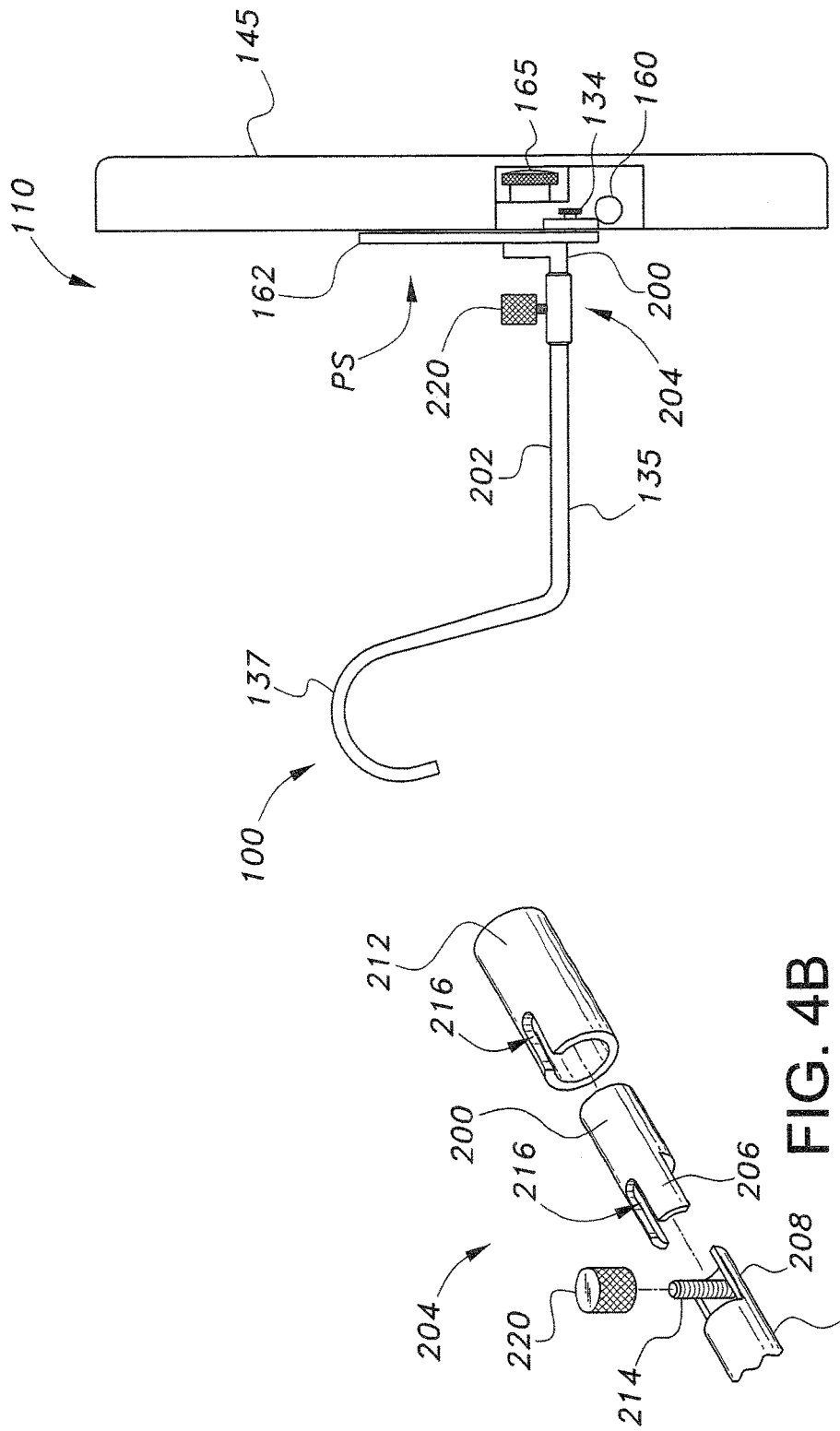

OCCLUSAL CANTING IDENTIFYING TOOL

BACKGROUND OF THE INVENTION

1. Field of the Invention

The present invention relates to dental instruments, and particularly to an occlusal canting identifying tool that provides an adjustable orthodontic tool for accurately measuring an occlusal cant.

2. Description of the Related Art

The occlusal plane is defined by an imaginary line that passes through the occlusal surfaces of teeth when the upper and lower jaws are closed. Typically, the orientation of this plane is evaluated using a tongue blade between the occlusal surfaces of the posterior teeth while the patient is closing his teeth. The orientation of the blade is then evaluated relative to the inter-pupillary line, the inter-pupillary line being an imaginary line that passes the center of the pupils of both eyes. These two lines should be parallel. Otherwise, any inclination represents an occlusal cant. An occlusal cant is one of the characteristics that must be evaluated during clinical examination in all patients seeking orthodontic treatment. It describes the upward and downward inclination of the orientation of occlusal plane in the transverse plane. Severe occlusal canting could result in facial asymmetry or malfunction, and the extent of canting of the occlusal plane determines the complexity of treatment, from simple orthodontic treatment to surgical intervention.

Currently, the commercially available devices relate the jaw (maxilla and/or mandible) to a reference point or plane, regardless of the orientation of the occlusal plane. This neglect for the occlusal plane orientation may render those devices inaccurate. Furthermore, any canting in the occlusal plane is crucial and needs to be identified as early as possible, preferably in the diagnostic phase of orthodontics.

Thus, an occlusal canting identifying tool solving the aforementioned problems is desired.

SUMMARY OF THE INVENTION

The occlusal canting identifying tool includes a frame having an elongated horizontal portion and a pair of parallel side arms movably attached to the horizontal portion at opposite ends thereof. The tool further includes a vertical arm centrally positioned on the front of the horizontal portion and a measuring assembly positioned on the rear of the horizontal portion. The measuring assembly includes a protractor rotatably attached to the rear of the horizontal portion, the protractor being configured to rotate on a horizontal axis in relation to the horizontal portion, and a bite plate connected to the protractor, the bite plate being adjustable forward and backward in relation to the protractor. The patient is instructed to bite on the bite plate, and if occlusal canting is present, the degree of canting is quantified by rotation of the protractor.

These and other features of the present invention will become readily apparent upon further review of the following specification and drawings.

BRIEF DESCRIPTION OF THE DRAWINGS

FIG. 4A: is a side view of the occlusal canting identifying tool according to the present invention.

FIG. 4B: is an exploded view of an interior tube used in conjunction with an external tube of a telescoping side arm of the occlusal canting identifying tool, according to the present invention.

Similar reference characters denote corresponding features consistently throughout the attached drawings.

DETAILED DESCRIPTION OF THE PREFERRED EMBODIMENTS

Figure 1:
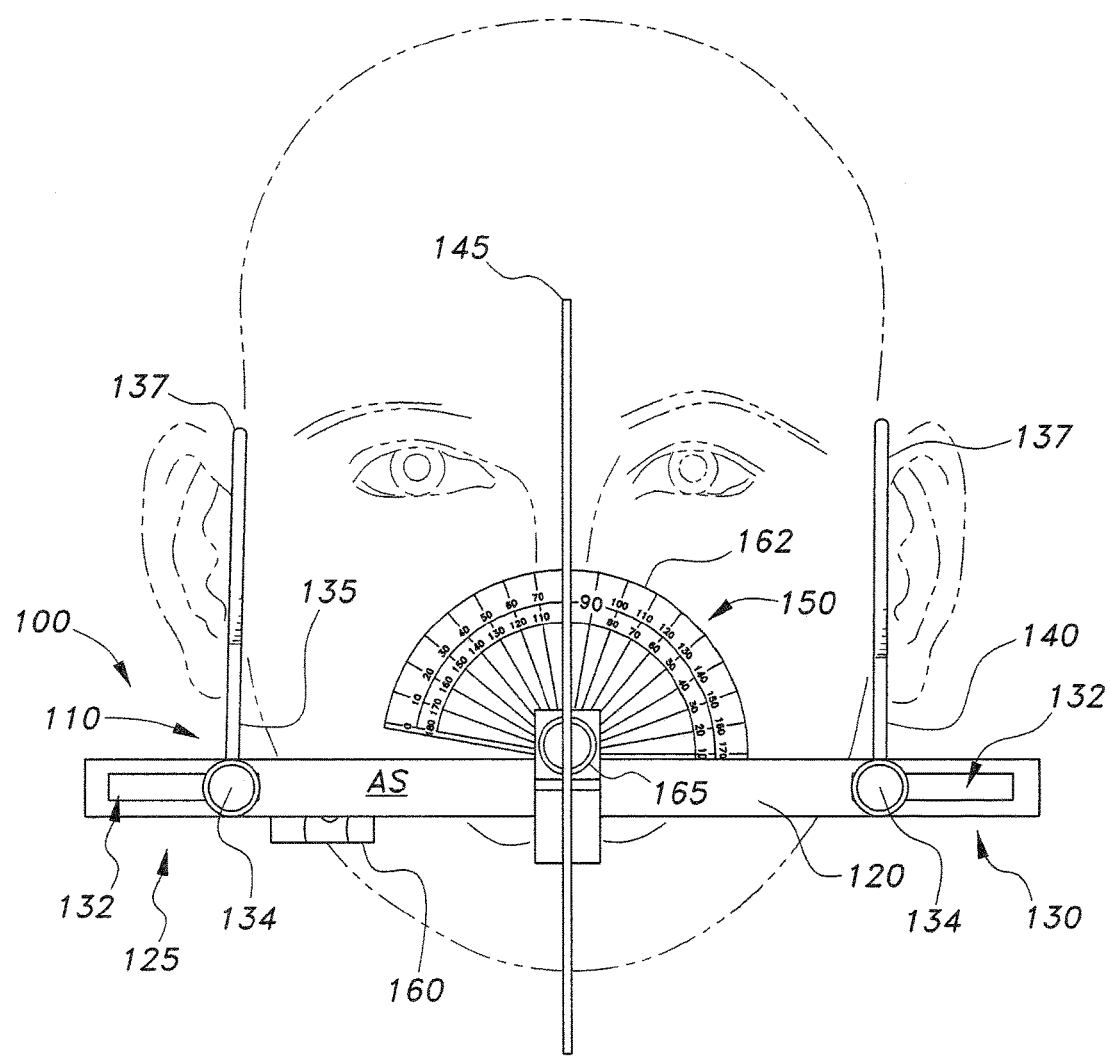
FIG. 1 is an environmental perspective view of an occlusal canting identifying tool according to the present invention, showing the tool in use.

Referring to FIG. 1, the occlusal canting identifying tool 100 is configured for identifying and quantifying the amount of occlusal canting so that the correct orthodontic intervention can be determined. The tool 100 can be made from any suitable material that can be disinfected and/or sterilized, and may allow orthodontists to predict the outcome of the orthodontic intervention and to discuss the effects of the canting with a patient at a much earlier stage in the treatment process. Further, the tool 100 may allow for a more accurate determination of the amount of canting in degrees, by measuring the cant in a transverse plane in relation to a reference plane, thereby eliminating the vague classification of occlusal canting into mild, moderate, or severe.

Figure 2:
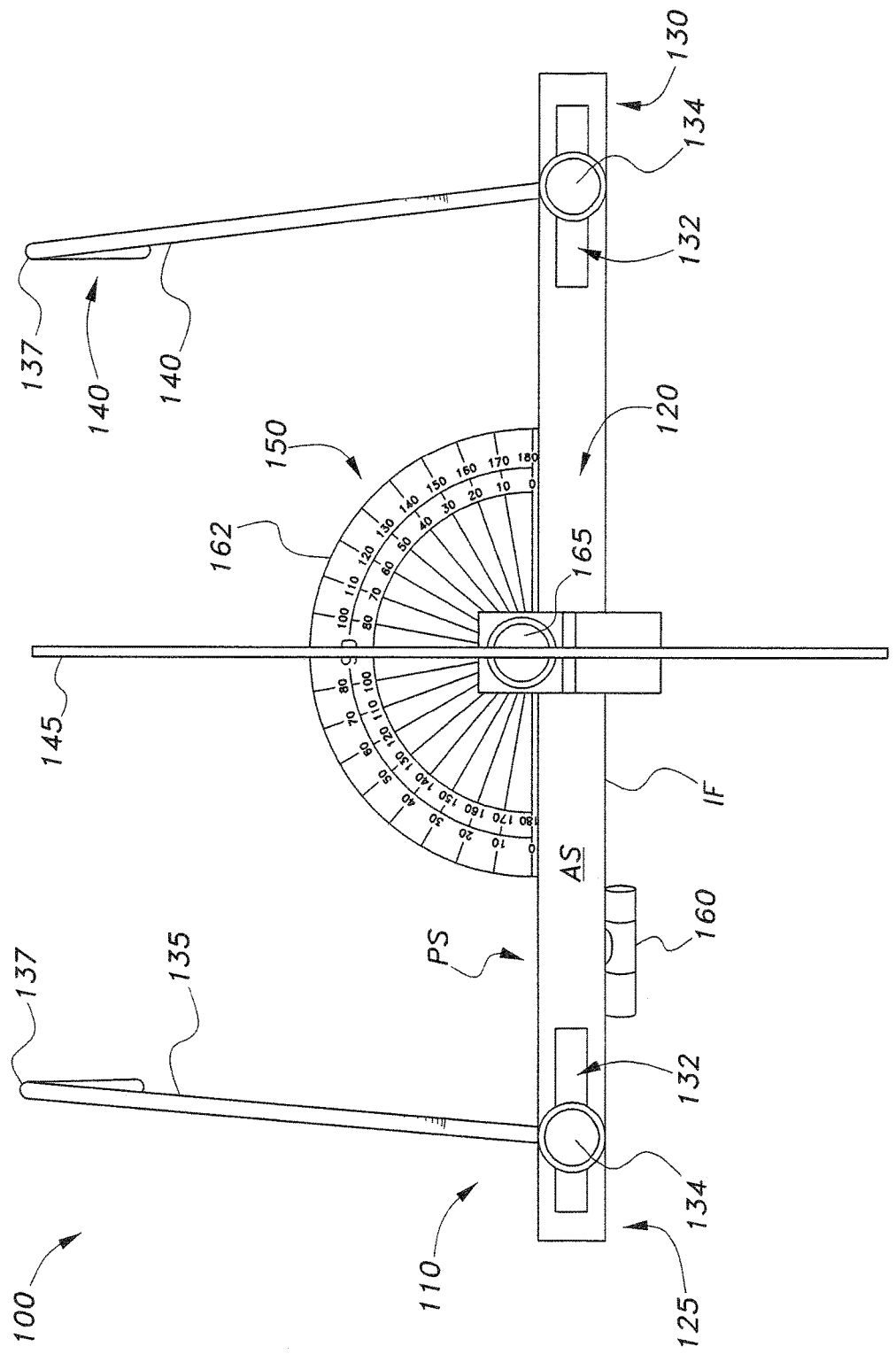
FIG. 2 is a front view of the occlusal canting identifying tool of FIG. 1.
Figure 3:
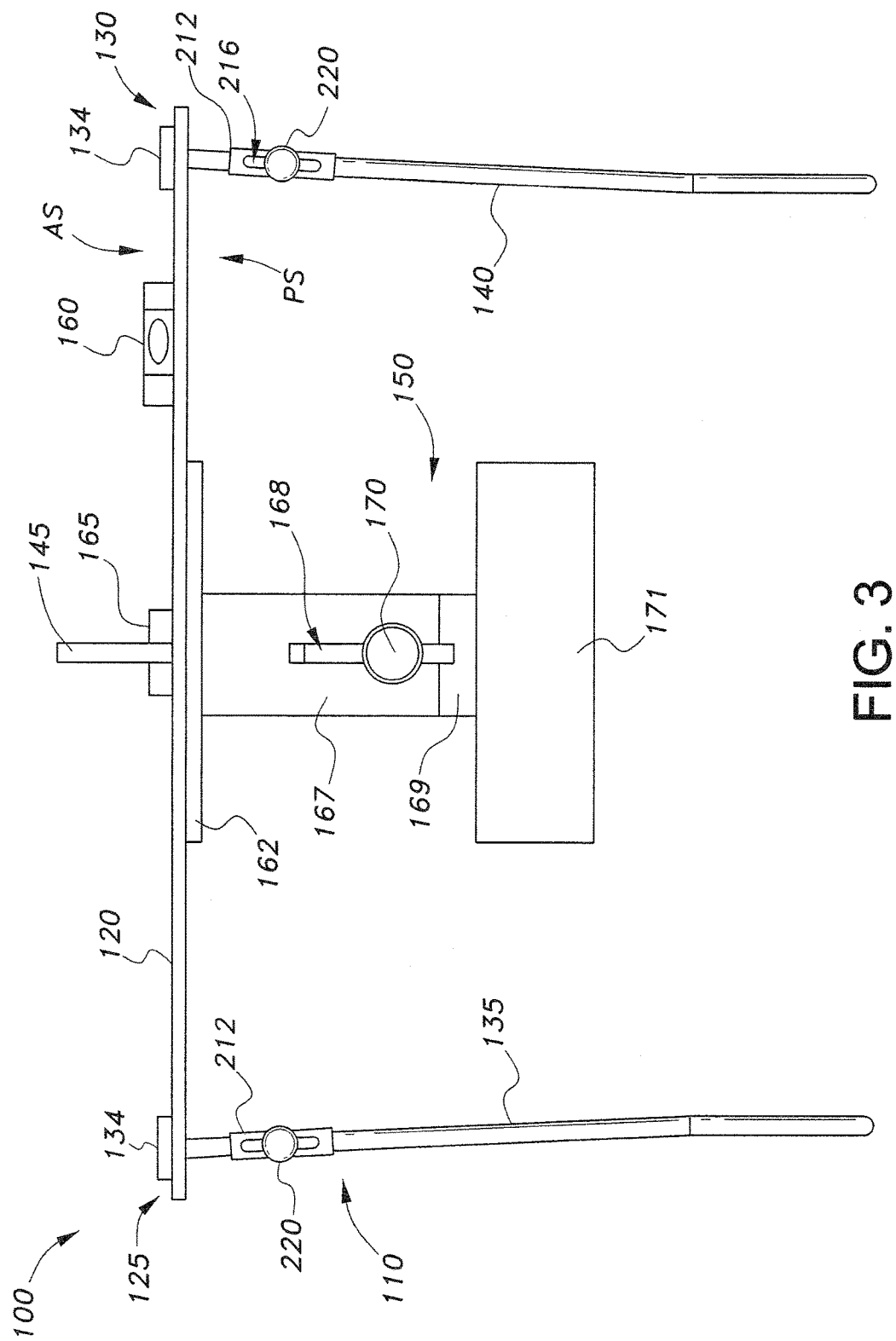
FIG. 3 is a top view of the occlusal canting identifying tool of FIG. 1.

As shown in FIGS. 1 and 2, the tool 100 includes a frame 110 having an elongated horizontal portion 120 (which may be a plate) including a first end 125 and an opposing second end 130, and two parallel side arms 135, 140 (analogous to the temple pieces of eyeglasses) attached to the posterior side PS of the horizontal portion 120 of the frame 110 and extending rearward therefrom substantially in the occlusal plane and then tilting upward, terminating in curved hook end portions 137 adapted for engaging a patient's ears, as best seen in FIGS. 1 and 4A. The tool 100 also includes a vertical arm 145 centrally positioned on the anterior side AS of the horizontal portion 120 of the frame 110 and extending upward and orthogonal to the horizontal portion. A measuring assembly 150 is pivotally mounted on the posterior side PS of the horizontal portion 120 of the frame 110. The tool 100 may also have a leveling device 160, such as a spirit level, positioned on the bottom or inferior border IF of the horizontal portion 120 of the frame 110. The leveling device 160 is configured for orienting the tool 100 parallel to the true horizontal plane of the floor.

As discussed herein, the horizontal portion 120 of the frame 110 represents the horizontal plane. The first end 125 and the opposing second end 130 of the horizontal portion 120 of the frame 110 each include a horizontal slot 132 configured for receiving a fastener 134, such as a thumbscrew. The fasteners 134 releasably secure the first side arm 135 and the second side arm 140 to the horizontal portion 120 via the slot 132. This allows the side arms 135, 140 to be adjusted laterally to accommodate the width of the patient's head.

Each of the side arms 135, 140 has an anterior portion 200 and a posterior portion 202 joined by a telescoping joint 204. The telescoping joint 204 includes an upper semi-cylindrical shell 206, which is concave downward, extending rearward from the anterior portion 200, a lower semi-cylindrical shell 208 extending forward from the posterior portion 202, and an external tubular sleeve 212 housing the telescoping joint 204. The lower semi-cylindrical shell 208 has a threaded post 214 or stud fixed to the shell 208 and extending upward therefrom. Both the upper semi-cylindrical shell 206 and the external sleeve 212 have a slot 216 defined therein, the threaded post 214 extending through and slidable in the slots 216. A knurled nut 220 is tightened on the post 214 to selectively clamp the upper and lower semi-cylindrical shells 206, 208 together. In this way, the length of each side arm 135, 140 can be adjusted by loosening the nut 220, sliding the upper and lower semi-cylindrical shells 206, 208 relative to each other to shorten or lengthen the side arm 135, 140, sliding the external sleeve 212 to conceal and protect the joint 204, and tightening the nut 220 to selectively clamp the shells 206, 208 together and fix the length of the side arm. Since the side arms 135, 140 can be adjusted laterally for the width of the patient's head and adjusted front to back for the position of the patient's ears, the tool 100 is adjustable for use with both adults and children.

The measuring assembly 150 is selectively attached to the horizontal portion 120 of the frame 100 by a thumbscrew 165. The measuring assembly 150 includes two layered sliding sheets or plates defining an adjustable length spindle, a protractor 162 attached to the upper sliding sheet 167, and a bite plate 171 attached to the lower sliding sheet 169. An adjusting screw 170 extends through a slot 168 in the upper sliding sheet 167 and is threadably attached to the lower sliding sheet 169. The screw 170 is loosened, and the bite plate 171 is slidably moved forward or backward to position the bite plate 171 between the patient's teeth when the patient bites down, and the screw 170 is tightened to fix the length of the measuring assembly 150. The protractor 162 is fixed to the upper sheet 167. When the device is in storage, the thumbscrew 165 may be tightened so that the 0°-180° line is parallel with the upper edge of the horizontal portion 120 of the frame 110 and the 90° hash mark is aligned with the vertical arm 145. When the tool 100 is used to measure occlusal canting, the thumbscrew 165 is loosened so that the measuring assembly 150 pivots or rotates on the thumbscrew 165 as a unit when the patient bites down on the bite plate 171. If the patient's occlusal plane is canted, the degree of canting can be quantified directly by observing the degree of tilting of the 0°-180° line on the protractor 162 relative to the horizontal portion 120 of the frame 110, or by observing the angular difference of the 90° hash mark on the protractor 162 from the vertical arm 145.

In use, the lateral position and length of the side arms 135, 140 and the depth of the bite plate 171 are adjusted according to the patient's anatomical features. The device is placed on the patient's head with the vertical arm 145 aligned with the midline of the patient's face and the horizontal portion 120 of the frame 110 aligned substantially horizontally, being supported by the health care professional with the aid of the bubble or spirit level 160 (when so equipped), if necessary. The thumbscrew 165 is loosened so that the measuring assembly 150 is free to pivot or rotate with the bite plate 171 between the patient's upper and lower teeth, and the patient is instructed to bite down on the bite plate 171. If occlusal canting is present, the degree of canting can be quantified by observing the degree of rotation of the protractor 162.

It is to be understood that the present invention is not limited to the embodiments described above, but encompasses any and all embodiments within the scope of the following claims.

We claim:
1. An occlusal canting identifying tool comprising:
a frame having:
  i) an elongated horizontal portion, the elongated horizontal portion having an anterior side and a posterior side, the elongated horizontal portion further including a first end portion and an opposing second end portion, wherein the first end portion and the second end portion each includes a horizontal slot defined therein;
  ii) a pair of parallel side arms, each is releasably secured to and extending rearwardly from the respective first and second end portions of the elongated horizontal portion via a thumbscrew extending through the respective horizontal slot, each of the side arms terminating in an ear hook adapted for supporting the frame on a patient's ears, wherein the thumbscrew allows said each side arm to be laterally adjustable along and relative to the respective horizontal slot to accommodate the patient's head width;
  iii) a vertical arm centrally positioned on the anterior side of the elongated horizontal portion, the vertical arm being adapted for alignment with the patient's facial midline; and
a measuring assembly rotatably attached to the posterior side of the elongated horizontal portion of the frame and extending rearwardly therefrom, the measuring assembly having:
  i) a spindle having an adjustable length, a front end, an opposing rear end, and a main central longitudinal axis extending along said adjustable length between said front and rear ends;
  ii) a protractor vertically and centrally fixed to the spindle at a front end portion of the spindle such that the protractor is positioned vertically upward from the spindle and normal to the main central longitudinal axis of the spindle;
  iii) a bite plate horizontally and centrally fixed to the spindle at a rear end portion of the spindle; and
  iv) a main thumbscrew attaching the front end of the spindle to the elongated horizontal portion of the frame, wherein the spindle is positioned centrally to the elongated horizontal portion and aligned with the vertical arm such that the main central longitudinal axis of the spindle is normal to the vertical arm; the measuring assembly being selectively rotatable about the main thumbscrew when the main thumbscrew is loosened and selectively precluded from rotation when the main thumbscrew is tightened, the measuring assembly rotating as a unit;
wherein when in use, the bite plate is configured to be inserted in the patient's mouth with the vertical arm being aligned to the patient's facial midline; and as the patient bites down on the bite plate, and with the main thumbscrew loosened, the measuring assembly is rotatable about the main thumb screw, allowing for quantification of occlusal canting by observing a degree of rotation of the protractor relative to the vertical arm.

2. The occlusal canting identifying tool according to claim 1, further comprising a spirit level mounted on the elongated horizontal portion of said frame.

3. The occlusal canting identifying tool according to claim 1, wherein each of said side arms comprises an anterior portion, a posterior portion, and an adjustable telescoping joint connecting the anterior portion to the posterior portion, allowing each of said side arms being adjustable in length.

4. The occlusal canting identifying tool according to claim 1, wherein said adjustable length spindle comprises:
a lower sliding sheet forming the rear end portion, the bite plate being mounted on the lower sliding sheet;

an upper sliding sheet forming the front end portion and slidably overlapping the lower sliding sheet, the upper sheet having a slot defined therein, the protractor being mounted on the upper sliding sheet; and a fastener insertable through the slot and selectively securing the upper sliding sheet to the lower sliding sheet to adjust the adjustable length of the spindle.

* * * * *